(12) United States Patent
Lacey et al.

(10) Patent No.: US 11,717,636 B2
(45) Date of Patent: Aug. 8, 2023

(54) ANESTHESIA VAPORIZER SYSTEM HAVING A VARIABLE VOLUME RESERVOIR

(71) Applicant: GE Precision Healthcare LLC, Wauwatosa, WI (US)

(72) Inventors: Joseph James Lacey, Madison, WI (US); Brady Weigel, Madison, WI (US); Thomas Bender, II, Madison, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 837 days.

(21) Appl. No.: 16/589,976

(22) Filed: Oct. 1, 2019

(65) Prior Publication Data

US 2021/0093826 A1    Apr. 1, 2021

(51) Int. Cl.
*A61M 16/18* (2006.01)
*A61M 16/01* (2006.01)
*A61M 16/10* (2006.01)

(52) U.S. Cl.
CPC .......... *A61M 16/183* (2013.01); *A61M 16/01* (2013.01); *A61M 16/104* (2013.01); *A61M 16/1005* (2014.02); *A61M 2202/0208* (2013.01); *A61M 2202/0283* (2013.01)

(58) Field of Classification Search
CPC .. A61M 16/183; A61M 16/01; A61M 16/104; A61M 16/1005; A61M 16/18; A61M 16/0081; A61M 2202/0208; A61M 2202/0283; A61M 5/148; A61M 5/1483; A61M 5/1486; A61M 5/152; A61M 5/155; B65D 2583/005
See application file for complete search history.

(56) References Cited

U.S. PATENT DOCUMENTS

| | | | | | |
|---|---|---|---|---|---|
| 2,842,123 | A | * | 7/1958 | Rundhaug | A61M 5/1486 604/141 |
| 3,894,538 | A | * | 7/1975 | Richter | A61M 5/14276 204/627 |
| 5,163,909 | A | * | 11/1992 | Stewart | A61M 5/1486 604/131 |
| 5,505,236 | A | * | 4/1996 | Grabenkort | B65D 47/38 141/382 |
| 6,406,458 | B1 | * | 6/2002 | Tillander | A61M 5/1483 604/246 |
| 6,878,133 | B2 | * | 4/2005 | Ahlmen | A61M 16/183 604/246 |
| 2002/0157670 | A1 | * | 10/2002 | Kullik | A61M 16/18 604/251 |
| 2009/0165787 | A1 | * | 7/2009 | Ahlmen | A61M 16/18 128/203.14 |

(Continued)

Primary Examiner — Colin W Stuart
Assistant Examiner — Douglas Y Sul

(57) ABSTRACT

An anesthesia vaporizer system includes a sump chamber, a variable volume reservoir within the sump chamber, and an anesthetic vaporizer. The variable volume reservoir is configured to contain anesthetic agent. A pressurized gas source is connected to the sump chamber and configured to maintain a constant pressure within the sump chamber to compress the variable volume reservoir to force the anesthetic agent through the anesthetic vaporizer, which vaporizes the liquid anesthetic agent for delivery to a patient.

19 Claims, 6 Drawing Sheets

(56) References Cited

U.S. PATENT DOCUMENTS

| | | | |
|---|---|---|---|
| 2012/0174925 A1* | 7/2012 | Tham | A61M 16/01 128/205.12 |
| 2012/0318263 A1* | 12/2012 | Jones | A61M 16/1075 128/203.12 |
| 2012/0318264 A1 | 12/2012 | Jones et al. | |
| 2019/0099581 A1 | 4/2019 | Kuzelka | |
| 2019/0117921 A1 | 4/2019 | Bender, II et al. | |

* cited by examiner

ANESTHESIA VAPORIZER SYSTEM HAVING A VARIABLE VOLUME RESERVOIR

BACKGROUND

This disclosure generally relates to anesthesia vaporizer systems and reservoirs therefor that contain a liquid anesthetic agent that is vaporized to deliver a gaseous anesthetic agent to a patient.

Anesthesia vaporizer systems are generally known and contain anesthetic agent that is vaporized within the system and delivered to the patient as a gaseous anesthetic agent. Anesthesia vaporizer systems generally include a vaporizer reservoir that contains a liquid anesthetic agent to be delivered to the patient after conversion to gas form, a vaporizing unit or system that vaporizes the liquid anesthetic agent, and a delivery system that delivers the gaseous anesthetic agent to the patient. Various prior art systems utilize various vaporization methods, including pneumatic over hydraulic delivery systems, wicks that evaporate the anesthetic agent into a surrounding gas stream, or heating systems that heat the anesthetic agent to cause vaporization to be mixed with other gases for delivery to the patient.

The agent is generally held to the vapor pressure of the agent which is a function of the agent temperature. When the anesthetic vaporizer system is to be filled or replenished with liquid anesthetic agent, the secondary reservoir is disconnected from the primary reservoir and is operative to provide anesthetic agent to the patient during refilling of the primary reservoir with liquid anesthetic agent. When the primary reservoir is disconnected from the secondary reservoir, it is depressurized in order to bring the primary reservoir to atmospheric pressure, whereupon a liquid anesthetic agent is poured or otherwise inserted into the primary reservoir. Once refilled, the driving pressure is restored in the primary reservoir, and the primary reservoir is reconnected to the secondary reservoir for continued operation.

Depending on the type of anesthetic agent being delivered, pressure within the vaporization chamber of an anesthetic vaporizer can be as high as 50 psi. Thus, in order to force agent from a reservoir in to the vaporization chamber, a pressure source is required. That pressure source is typically a pump. Prior art vaporizer systems typically include a pump configured to deliver pressurized liquid to the vaporizer and drive the agent through the vaporizer. The pump is typically configured to pump anesthetic agent from the reservoir and provide the agent at a predetermined pressure to a vaporization chamber.

Most vaporizers only have a single chamber and the pressure inside is dictated by the vapor pressure of the agent, which is a function of agent temperature. There are three commercial anesthetics used for vapor delivery Sevoflurane (SEVO), Isoflurane (ISO), and Desflurane (DES). Of those, ISO and SEVO vapor pressures are sub atmospheric at typical ambient temperatures of 20° C., and DES is typically maintained above ambient pressures.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an anesthesia vaporizer system includes a sump chamber, a variable volume reservoir within the sump chamber, and a vaporizer. The variable volume reservoir is sealed from the sump chamber and configured to contain anesthetic agent. A pressurized gas source is connected to the sump chamber and configured to maintain a constant pressure within the sump chamber to compress the variable volume reservoir at the constant pressure to force the anesthetic agent through the vaporizer, which vaporizes the liquid anesthetic agent for delivery to a patient.

In one embodiment, an anesthesia reservoir for an anesthesia vaporizer system includes a sump chamber and a variable volume reservoir within the sump chamber, wherein the variable volume reservoir is sealed from the sump chamber and configured to contain liquid anesthetic agent. A pressurized gas valve is configured to connect a pressurized gas source to the sump chamber so as to maintain a constant pressure within the sump chamber to compress the variable volume reservoir within the sump chamber such that it forces the liquid anesthetic agent through an anesthetic vaporizer. A fill port is provided and configured to permit flow of liquid anesthetic agent from a liquid anesthetic agent source, such as a bottle, to refill the variable volume reservoir. A vent port is also provided and configured to vent gas from the sump chamber when the variable volume reservoir is refilled.

Various other features, objects, and advantages of the invention will be made apparent from the following description taken together with the drawings.

DETAILED DESCRIPTION

Figure 1:
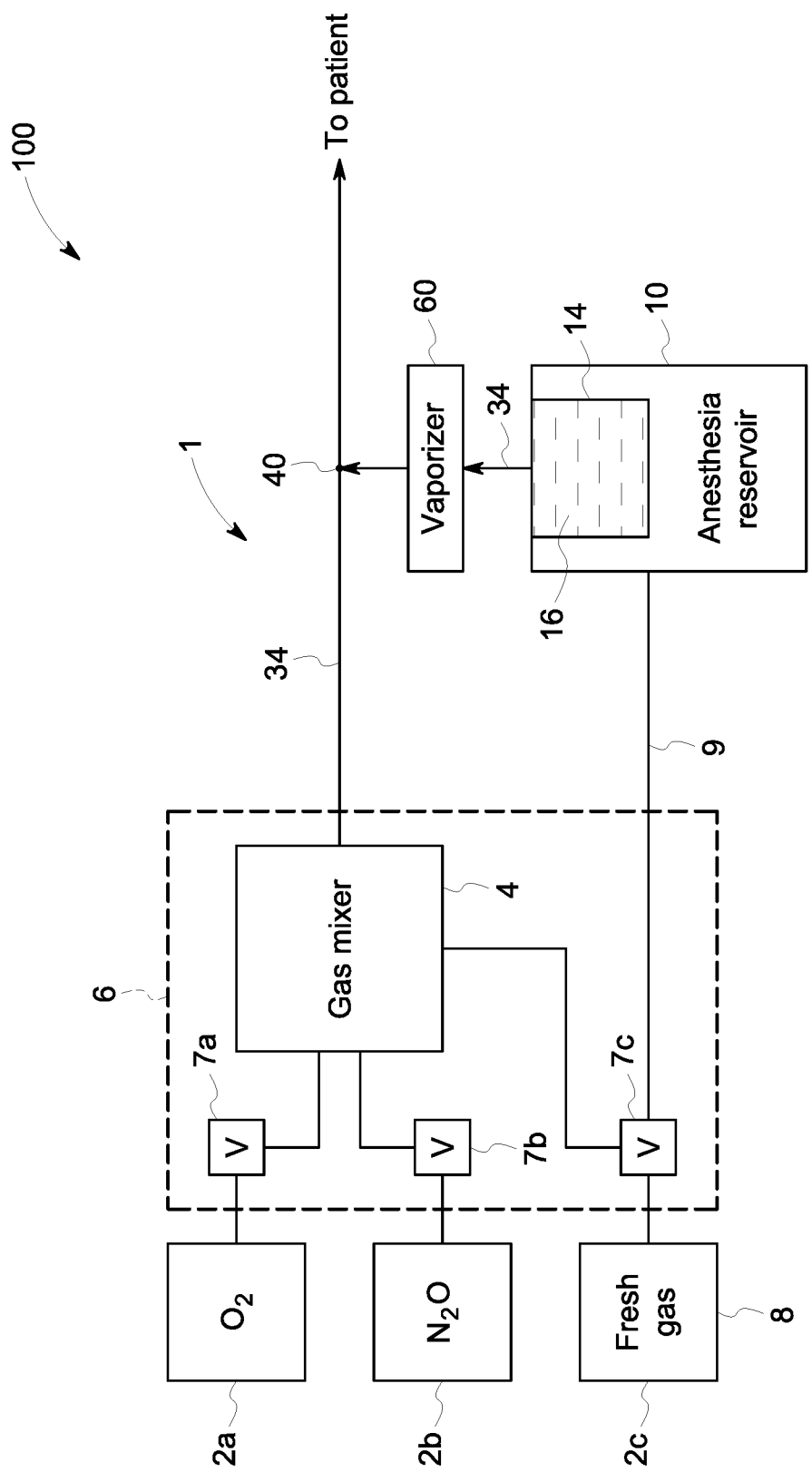
FIG. 1 schematically depicts an anesthesia vaporizer system according to the present disclosure.

Through their experimentation and research in the relevant field, the inventors have recognized a need for an improved vaporizer reservoir that eliminates the need for a pump to provide pressurized anesthetic agent to a vaporizer. The inventors have recognized that pumps are a major point of failure and cost for vaporizer systems, and further that pumps increase the size of vaporizer systems. In recognition of the foregoing challenges and problems, the inventors have endeavored to develop an anesthesia reservoir and associated anesthesia vaporizer system that eliminates the need for a pump to control pressure of the anesthetic agent. As a result of significant experimentation and research, the inventors developed the disclosed anesthesia vaporizer system and related method whereby a pressurized gas source is connected to the anesthesia reservoir and configured to maintain a constant pressure therein so as to maintain the anesthetic agent in a pressurized condition and to drive the anesthetic agent through the vaporizer. Thereby, the need for a liquid pump within the vaporizer system is eliminated.

In particular, the anesthesia reservoir disclosed herein includes a variable volume reservoir that is within a sump chamber. The variable agent reservoir is a sealed, compressible volume that is compressed by the constant pressure maintained within the surrounding rigid sump chamber. A pressurized gas source is connected to the rigid sump chamber such that the interior of the sump chamber is generally maintained at the pressure of the pressurized gas source. The variable volume reservoir is sealed from the gas portion of the sump chamber so that the anesthetic agent does not mix with the pressurized gas. Gas is provided to the sump chamber in order to maintain a constant pressure therein as anesthetic agent is evacuated from the variable volume reservoir and delivered to the patient. The variable volume reservoir is thus compressed and shrinks, or decreases in volume, as the anesthetic agent is pushed out. The variable volume reservoir thus allows for delivery of anesthetic agent at a constant pressure.

In view of the problems and challenges with current anesthesia vaporizer systems recognized by the inventors, they developed the disclosed design that enables pressurizing the primary chamber to use as means of driving a pressurized liquid through an injector. The disclosed system utilizes existing pressurized gas infrastructures to generate a constant driving pressure for the vaporizer system. The inventors have further recognized that the pressurized sump chamber needs to be refillable and work with existing anesthesia refill bottle assemblies. Pressurizing the chamber could cause issues with ISO and SEVO, where bottles provided by drug manufactures use a screw on valve adapter. Thus, the disclosed system is also configured such that when the valve adapter is unscrewed, it does not cause anesthetic gas to vent into the surrounding atmosphere. Thus, certain embodiments are designed such that the chamber pressure can be relieved for filling. This enables the use of existing anesthesia refill bottles, including existing ISO and SEVO bottles, with the disclosed system and avoids the need for providing additional valves.

FIG. 1 is a schematic diagram of an exemplary anesthesia system 100 comprising a vaporizer system 1. The system generally includes an anesthesia reservoir 10 providing liquid anesthetic agent to a vaporizer 60. The vaporizer system 1 is configured to vaporize the liquid anesthetic agent 16 so as to introduce the vaporized anesthetic agent into a pneumatic circuit delivering gaseous anesthetic to the patient. Thus, the vaporizer system 1 is provided within an anesthesia system 100.

The anesthesia system 100 includes an anesthesia machine 6, a plurality of gas sources 2a-2c, and an anesthetic vaporizer system 1. The anesthesia machine 6 is simplified for illustrative purposes and it should be appreciated that many types of anesthesia machines are well known in the relevant art and may be implemented with the disclosed anesthesia vaporizer system 1. The anesthesia machine 6, includes a gas mixture adapted to received various medical gasses from the gas sources 2a-2c. The anesthesia machine 6 further includes a variety of valves 7, including one or more valves 7a-7c for selected or controlling the flow of gas from the respective gas source 2a-2c. The gas mixer 4 combines the gasses from the various gas sources to form a carrier gas that flows to the patient via a pneumatic circuit 36.

The gas sources 2a-2c may take any form appropriate for medical gas storage. In one embodiment, gas sources 2a-2c are centrally located storage tanks configured to supply medical gas to multiple anesthesia machines and multiple hospital rooms. In other embodiments, the gas sources 2a-2c may be smaller room-specific storage tanks or storage tanks associated with a single anesthesia machine. In the various embodiments, gas storage tanks are generally pressurized to facilitate the transfer of medical gas to a receiving source, such as the anesthesia machine 6. In the depicted example, the gas sources include a pressurized oxygen ($O_2$) tank 2a, a pressurized nitrous oxide ($N_2O$) tank 2b, and a pressurized fresh gas (air) tank 2c. However, it should be appreciated that other storage devices and other types of gas may alternatively be implemented. Additionally, other valves may be implemented inside or outside of the anesthesia machine 6 in order to control the flow of gas from the storage devices 2a-2c to the anesthesia machine 6, such as a gas shutoff valve for each gas source.

In the depicted example, the fresh gas source 2c provides a pressurized gas source 8 that feeds a pressurized fresh gas line 9 from the anesthesia machine that is used to pressurize the anesthesia reservoir 10 and drive the liquid anesthetic through the anesthesia vaporizer 60, such as an injector. For example, a fresh gas line 9 of a typical anesthesia machine has a pressure of 70 psi, making it possible to use the fresh gas line to drive anesthetic agent from the reservoir 10 to the vaporization chamber. The pressure within the vaporization chamber of a typical anesthetic vaporizer may be as high as 50 psi. In various embodiments of the disclosed system, the pressurized gas source 8 may provide a pressure in the range of 42 psi to 89 psi, and thus the pressure within the reservoir 10 may be the same. Flow of pressurized gas 8 into the sump chamber 12 may be provided and/or controlled by a pressurized gas valve 24. Depending on the configuration of the pressurized gas source 8 and the overall configuration of the vaporizer system 1, in various embodiments the pressurized gas valve 24 may be an entirely mechanical valve that is manually or automatically mechanically actuated, or may be an electromechanical valve that is electrically actuated via one or more actuators. Certain electrically actuated embodiments such as described below with respect to FIG. 3.

The pressurized gas source provides a mechanism to drive the flow of liquid anesthesia. This eliminates and replaces the need for a pump and thereby provides a more efficient and more reliable vaporizer system. Moreover, the vaporizer system can be made smaller by the elimination of the pump. Since the pressurized fresh gas source 2c is readily available, no additional mechanisms or systems are necessary in order to drive the anesthetic agent other than a simple gas line 9 that connects the pressurized fresh gas source 2c to the anesthesia reservoir 10. In other embodiments, however, different pressurized gas sources may be utilized to drive the liquid anesthesia delivery, and may generally be any pressurized gas source. For example, the pressurized $O_2$ source 2a or $N_2O$ source 2b may instead be used. In still other embodiments, a gas canister or dedicated pressurized gas tank may be utilized to drive the liquid anesthesia through the vaporizer 60, such as an injector. For example, a $CO_2$ canister may be connected at the pressurized gas inlet of the anesthesia reservoir 10 which may be replaced when the pressure within the canister falls below a threshold.

The vaporizer system 1 includes an anesthesia reservoir 10 providing liquid anesthetic agent 16 to a vaporizer 60. The vaporizer 60 converts the liquid anesthetic agent to a vaporized anesthetic agent, which gets introduced to the carrier gas in the pneumatic circuit 36 at an inlet 40. The vaporized anesthetic agent mixes with the carrier gas and is then delivered to the patient. Although the vaporizer system 1 is schematically depicted as being a separate component of the anesthesia system 100, it should be appreciated that it may alternatively be incorporated in to the design of the anesthesia machine 6. In various embodiments, the vaporizer 60 may include a flow regulator, or injector, and a vaporization chamber, wherein the flow regulator regulates flow from the pressurized delivery line 34 to the vaporization chamber. Various vaporization chambers and flow regulation elements are utilized in the relevant art and a person of ordinary skill in the art will understand, in view of the present disclosure that any number of such flow regulation and vaporization elements may be incorporated in the disclosed system.

Figure 2A:
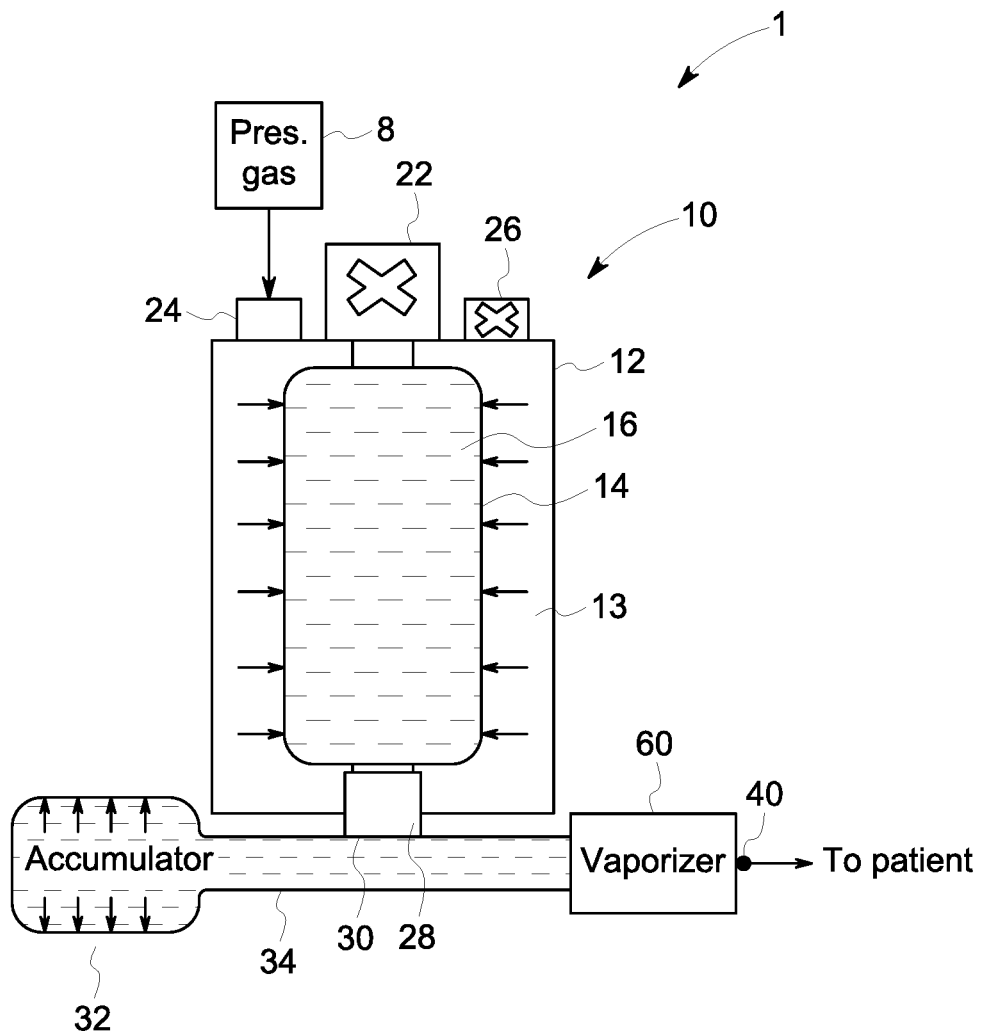
FIGS. 2A-2B depict an anesthesia reservoir and represent an operation state where anesthetic agent is delivered from the anesthesia reservoir to a vaporizer.
Figure 2B:
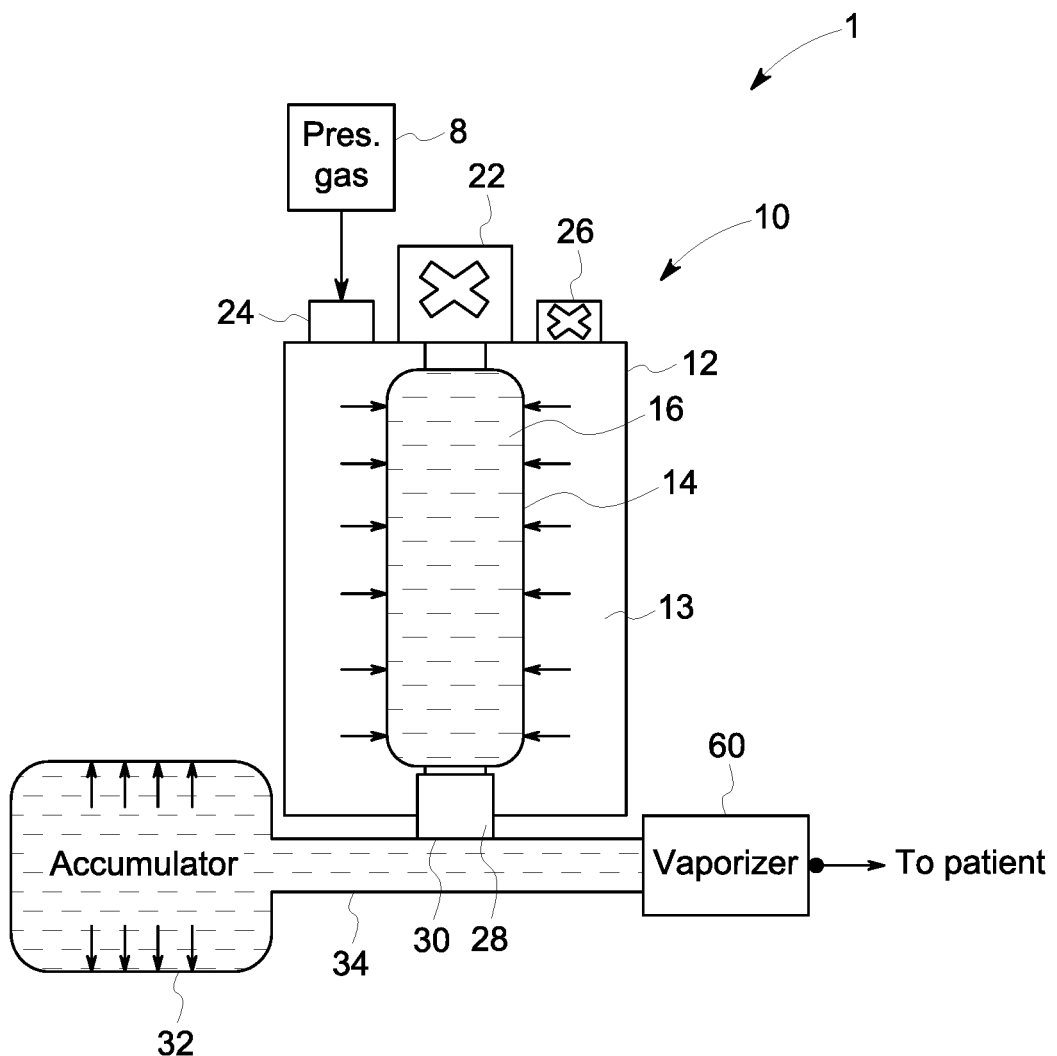
Figure 3:
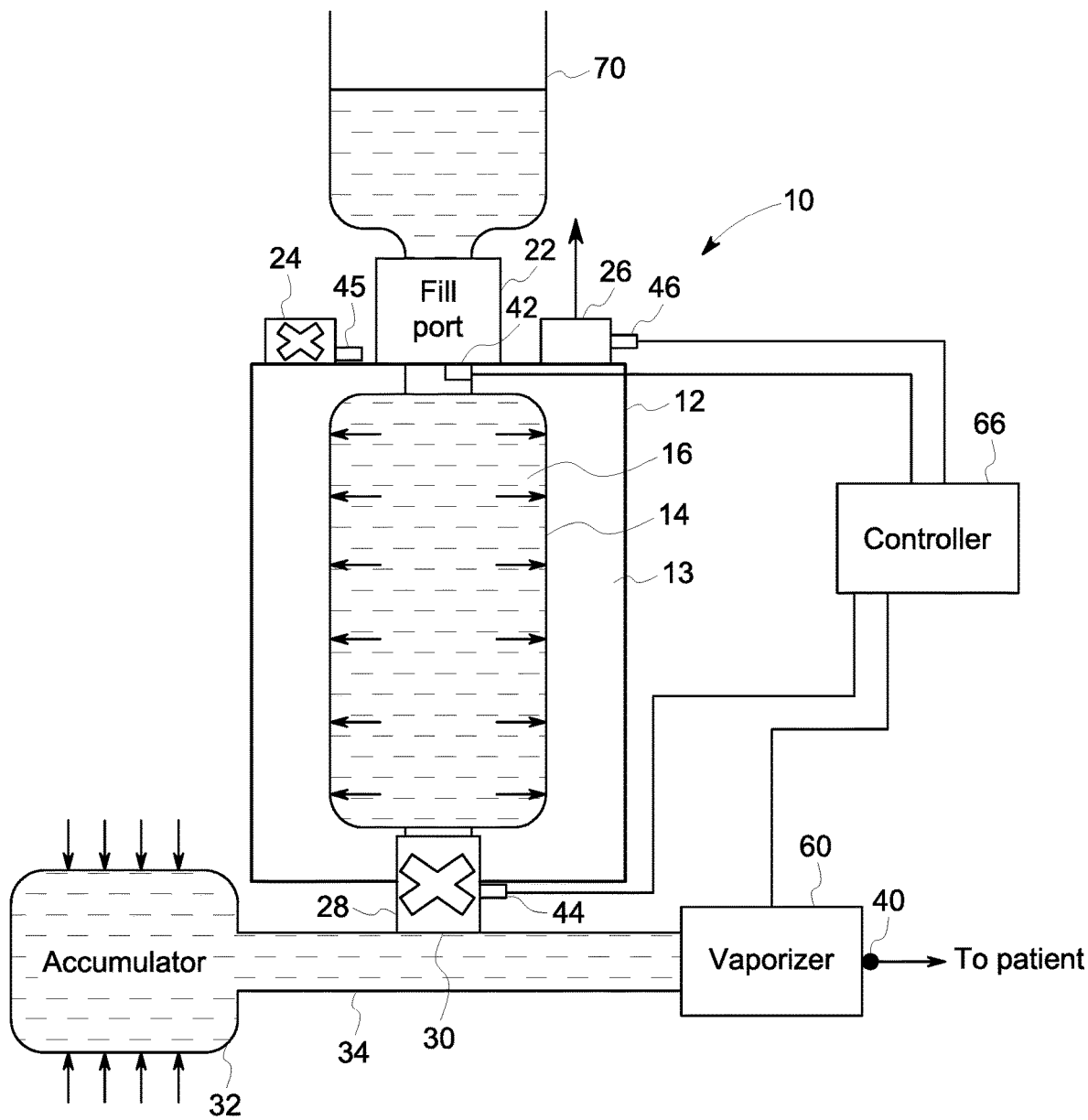
FIG. 3 depicts another embodiment of an anesthesia reservoir which is in a refill state where the reservoir is being refilled with anesthetic agent.
Figure 4:
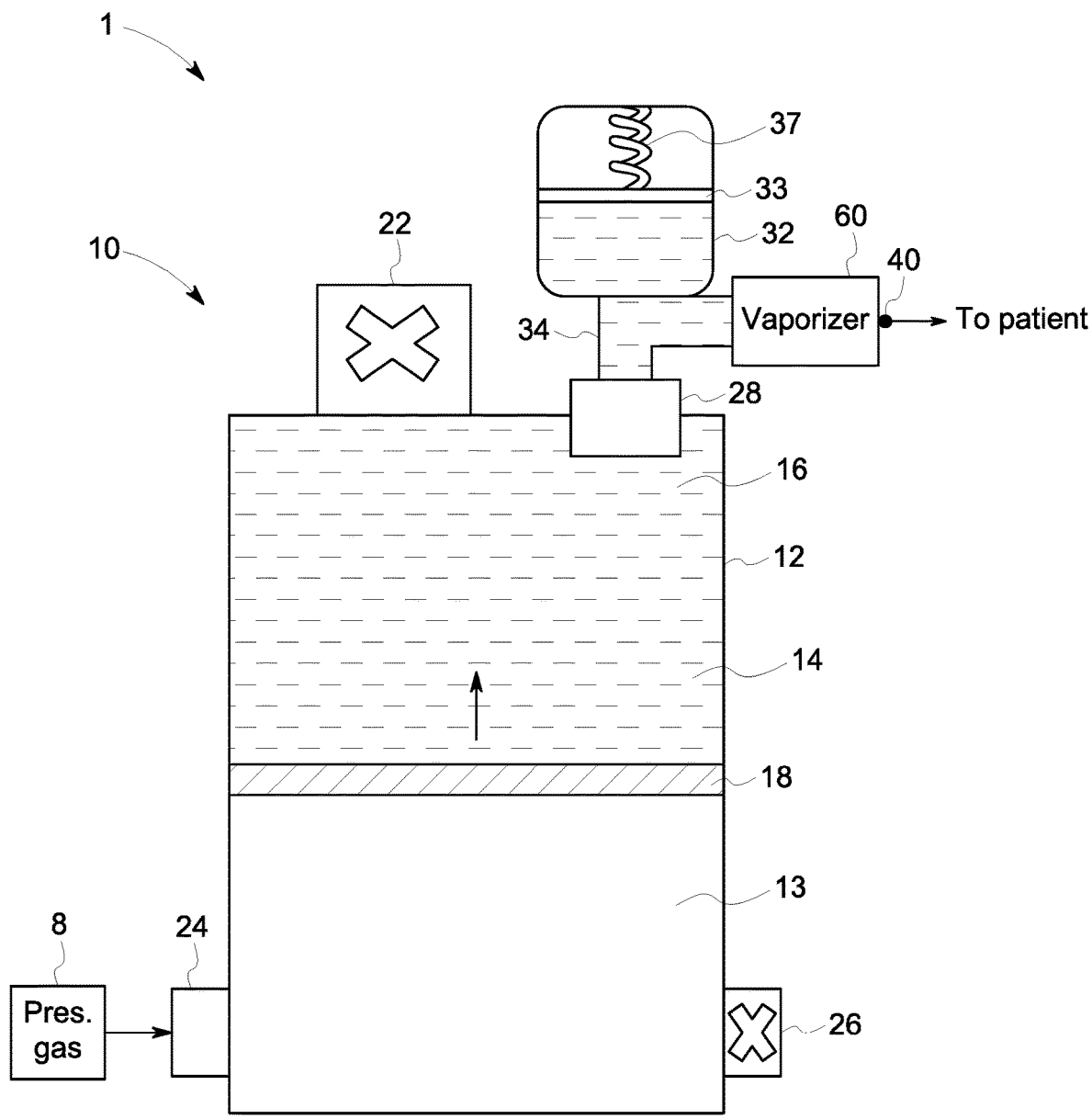
FIG. 4 depicts another embodiment of an anesthesia reservoir, which is shown in an operating state where anesthetic agent is being delivered from the anesthesia reservoir to a vaporizer.

FIGS. 2A and 2B depict one embodiment of a vaporization system 1 having an anesthetic reservoir 10 in accordance with the present disclosure. FIGS. 3 and 4 depict additional embodiments of vaporizer reservoirs 10 and/or depict vaporizer reservoirs in varying states in accordance with the present disclosures. FIGS. 2A and 2B depict an anesthesia vaporizer system 1 where the anesthesia reservoir 10 is operating in a delivery state to deliver liquid anesthesia agent out of the reservoir volume to the vaporizer 60. The anesthesia reservoir 10 includes a sump chamber 12 and a variable volume reservoir 14 within the sump chamber that is configured to contain the liquid anesthetic agent 16. The variable volume reservoir 14 is refillable via the fill port 22, such as from a standard anesthetic bottle. The variable volume reservoir 14 is compressible and gets compressed as the liquid anesthetic agent is delivered to the vaporizer 60. The sump chamber 12 is pressurized to a constant pressure by the pressurized gas source 8 connected thereto. A pressure equilibrium is reached between the variable volume reservoir 14, which is a sealed container containing the liquid anesthetic agent 16, and the surrounding environment of the cavity 13 within the rigid sump chamber 12.

As anesthetic agent is delivered to the gas delivery circuit 36, and thus delivered to the patient, the pressure in the variable volume reservoir 14 decreases. In order to maintain constant pressure in the cavity 13 within the sump chamber 12, gas gets added from the pressurized gas source 8. Where the pressurized gas source 8 is provided at a constant pressure, such as via a fresh gas line 9 from the anesthesia machine 6, the pressurized gas valve 24 may be a mechanically actuated valve that remains open such that the pressure from the pressurized gas source 8 is transferred and maintained within the sump chamber 12.

The variable volume reservoir 14 connects to the vaporizer 60 and provides liquid anesthetic agent through the anesthetic line 34. In certain embodiments, an accumulator 32 is connected to the anesthetic line 34 which accumulate liquid anesthetic agent 16 during the delivery state. Namely, the anesthetic line 34 and accumulator 32 may be connected to the variable volume reservoir 14 such that the pressure in the anesthetic line 34 and the accumulator 32 equalizes with the pressure in the variable volume reservoir 14. For example, an inlet 30 between the variable volume reservoir 14 and the pressurized anesthesia delivery line 34 may remain open during the delivery state. In that state, the accumulator 32 collects a volume of anesthetic agent which can then be used when the variable volume reservoir 14 is being refilled. This embodiment enables continued delivery of anesthetic agent to the patient while the variable volume reservoir 14 is being refilled such that agent delivery to the patient continues without interruption. This differs from current vaporizers, which typically suspend agent delivery to the patient while the sump is being filled.

As shown in FIGS. 2A and 2B, as the liquid anesthetic agent 16 is delivered out of the variable volume reservoir 14, the reservoir compresses and occupies less space inside the sump chamber 12. Pressurized gas from the pressurized gas source 8 is delivered to the sump chamber 12 in order to maintain a constant pressure therein. Once the variable volume reservoir 14 has been depleted of liquid anesthetic agent 16, or reaches a low volume threshold, the variable volume reservoir 14 is then refilled with liquid anesthetic agent. In order to facilitate refilling, the anesthetic reservoir 10 switches to a refilling state where a fill port 22 facilitates the insertion of liquid anesthetic agent from a fill source, such as a standard liquid anesthetic agent bottle, into the variable volume reservoir 14. FIG. 3 schematically depicts an embodiment of the anesthesia reservoir 10 in a refill state. In embodiments having an accumulator 32 on the anesthetic line 34, liquid anesthetic agent may continue to be delivered to the vaporizer 60 during the refill state where such delivery is provided by the accumulator 32. In other embodiments where an accumulator is not provided, delivery of the vaporized anesthetic may cease during the short refill.

In the depicted example, the anesthesia reservoir 10 is configured such that the pressurized gas valve 24 closes in the refill state and a vent port 26 opens to allow evacuation of the pressurized gas from inside the sump chamber 12. Thereby, expansion of the variable volume reservoir 14 is permitted. For example, the fill process may be a gravity-fed process where the liquid anesthetic agent source, such that the anesthetic agent bottle 70 is connected above the variable volume reservoir 14 and the fill port 22 opens to allow the anesthetic agent to drain from the bottle 70 into the variable volume reservoir 14 thereby causing the variable volume reservoir 14 to expand. In order to facilitate the refilling and expansion of the variable volume reservoir 14, the pressure within the cavity 13 of the sump chamber 12 must be significantly reduced, such as to atmosphere. In various embodiments, the vent port 26 may be vented to atmosphere or may vent to a secondary chamber. Where the pressurized gas source 8 is fresh gas, venting to atmosphere may be preferable. Where the pressurized gas source is a regulated gas that is not permitted to vent to atmosphere (e.g., into the atmosphere of the operating room), the vent port 26 may vent to a secondary chamber and/or to a scrubber that removes and/or contains the regulated gas. In various embodiments, the vent port may be a valve, such as a manually, mechanically, or electrically actuated valve. Similarly, the fill port 22 may be any type of valve, and various fill ports for liquid anesthesia reservoirs are well known in the relevant art.

To facilitate filling, a sump shut off valve 28 may be provided that stops the flow of liquid anesthetic agent from the variable volume reservoir 14 to the anesthetic line 34. The sump shut off valve may be any type of valve, which may be manually, mechanically, or electrically actuated. In one embodiment, one or more of the pressurized gas valve 24, vent port 26, and sump shut off valve 28 are electrically actuated. FIG. 3 depicts one such embodiment, where each valve is associated with an actuator 44-46 that electrically actuates the respective valve 24, 26, 28 as appropriate based on whether the anesthesia reservoir 10 is operating in the delivery state to deliver anesthetic agent to the vaporizer or in the refill state where it is getting refilled with liquid anesthetic agent. In the depicted embodiment, the actuators are controlled by a controller 66 based on the delivery state. For example, the controller 66 may be the controller for the vaporizer system 60, as shown in the diagram at FIG. 3, or may be a dedicated controller.

In one embodiment, the controller 66 may automatically select between the delivery state and the refill state based on input from the fill sensor 42. For example, the fill sensor 42 may sense whether a bottle 70 is connected to the fill port 22, or may otherwise sense whether anesthetic agent is being provided through the fill port 22. If a bottle 70 is connected and/or anesthetic agent is being delivered through the fill port 22, then the controller 66 may operate the valves in order to facilitate the refill state. In the refill state, the pressurized gas valve 24 is closed, the vent port 26 is open, and the sump shut off valve 28 is closed. The actuator 45 for the pressurized gas valve 24 is controlled to close the pressurized gas valve 24 to prevent the delivery of pressurized gas into the chamber cavity 13 during the refill process. The actuator 44 is controlled to close the sump shut off valve 28 in order to prevent the flow of anesthetic agent from the variable volume reservoir 14 to the pressurized anesthetic line 34 during the refill process. Then the vent port 26 is opened to release gas from the chamber cavity 13, and thus the actuator 46 is controlled to open the vent port 26, which reduces the pressure in the sump chamber so that the variable volume reservoir can expand as it refills. The fill port is then opened, which may be mechanically or electrically actuated in order to allow the flow of anesthetic agent 16 from the bottle 70 into the variable volume reservoir 14.

In other embodiments, the pressurized gas valve 24, vent port 26, and sump shut off valve 28 may be mechanically controlled and actuated. In one such embodiment, one or more of the pressurized gas valve 24 and the vent port 26 may be integrated with the fill port such that opening of the fill port 22 manually closes the pressurized gas valve 24 and/or manually opens the vent port 26. For example, the fill port 22 may be configured such that connection of a bottle 70 thereto pushes the pressurized gas valve in to the closed position and/or pushes the vent port 26 into the open position. To provide just one example, the system may be configured such that connection of a bottle to the fill port 22 manually actuates the pressurized gas valve into the closed position. A sensor 42 may also be provided which senses either the closing of the pressurized gas valve 24 or the connection of the bottle to the fill port 22. The controller 66 may be then be configured to control the actuator 44 to close the sump shut off valve 28 and then control the actuator 46 to open the vent port 26. In still other embodiments, one or more of the valves 22, 24, 26, 28 may require manual operation and actuation by an operator.

In the refill state, liquid anesthetic agent may be delivered from the accumulator 32 to the vaporizer 60. For example, the accumulator may be a variable volume reservoir as well where energy is stored during the accumulation process in the delivery state to push the liquid anesthetic agent through the vaporizer 60. For example, the accumulator 32 may be an expandable volume, such as an elastomeric balloon or a bellows. In one such embodiment, the accumulator will expand under the pressure (i.e., driven by the pressurized gas source) during the delivery state to store anesthetic agent and energy (e.g. due to expansion of the elastomeric material). Then, during the refill state, the elastomeric balloon will contract and force the liquid anesthetic agent 16 stored therein toward and through the vaporizer 60. Thereby, agent can still be delivered to the patient during the refill process.

In another embodiment, the accumulator may include a spring loaded piston, which is exemplified in FIG. 4. For example, a constant spring 37 may be connected to the piston 33 such that a constant force is placed on the liquid anesthetic agent that is less than the constant pressure within the sump chamber 12. Thus, during the delivery state, the piston 33 will be moved to compress the constant spring 37 and permit the accumulator 32 to fill with anesthetic agent. Then during the refill state, the spring 37 will exert the constant force on the piston 33 to push the liquid anesthetic agent out of the accumulator 32 and through the vaporizer 60 at a constant pressure. In certain embodiments, the vaporizer 60 may be configured to adjust operation during the refill state so that a consistent amount of anesthetic agent is vaporized during the refill state as was being vaporized at the conclusion of the delivery state. For example, where the constant pressure from the spring 37 is lower than the pressure maintained by the pressurized gas during the delivery state, the flow regulator may adjust operation to compensate for the lower pressure. For example, a pressure transducer may be provided to measure pressure in the accumulator 32, or a position sensor may be configured to measure a position of the piston 33. The pressure information and/or the piston position information may be provided to the controller 66, which can then control the vaporizer 60 accordingly.

In other embodiments, the pressure within the accumulator 32 may be managed by other means. To provide an additional example, a heater may be provided that heats the anesthetic agent in the area of the heater, providing expansion. For example, the heater may be a heating element on a top portion of the accumulator that is configured to heat and vaporize some of the agent in the accumulator. The gaseous anesthetic agent will create increasing pressure within a rigid accumulator vessel. The accumulator can be configured such that the liquid, which will stay in the bottom of the vessel due to gravity, will be forced out of the accumulator 32 and toward the vaporizer 60. This may work particularly well for certain volatile anesthetic agents, such as Desflurane that easily vaporize at the relevant pressure and temperature ranges sustained within the accumulator. In a related embodiment, the accumulator 32 may contain a balloon surrounding the heating element where the heating element causes the balloon to expand at a predetermined rate.

In various embodiments, the variable volume reservoir 14 may be any of various types of compliant chambers. For example, the variable volume reservoir 14 may be a bag or an elastomeric balloon that expands and contracts within the sump chamber 12. In another embodiment, the variable volume reservoir 14 may be a bellows that expands and contracts, such as moves up and down, within the sump chamber 12. In still other embodiments, the variable volume reservoir 14 may be provided by a moving divider that is provided within the sump chamber 12 and creates two variable volume sub chambers that are reciprocally connected. FIG. 4 provides an example of one such embodiment, wherein the moving divider is a piston 18 sealably suspended within the sump chamber 12 so as to divide the sump chamber 12 into two separate spaces, one being the variable volume reservoir. The pressurized gas source 8 is connected within the pressurized chamber cavity 13 on the first side of the piston 18, and a chamber containing the liquid anesthetic agent, providing the variable volume reservoir 14' is on the other side of the piston 18. The piston 18 is configured to provide minimal resistance so that is moves toward the outlet as liquid anesthetic agent 16 is forced through the vaporizer 60. Namely, the piston 18, or other movable divider, is configured such that the pressure within the chamber cavity 13 is transferred effectively to the variable volume reservoir 14. In a similar embodiment, the movable divider (e.g., piston 18) is driven up and down by a bellows connected to the pressurized gas source.

As shown in the example, the pressurized gas valve 24 and the vent port 26 are provided on the gas chamber cavity 13 side of the divider, while the fill port 22 and the sump shut off valve 28 are provided on the variable volume reservoir 14' side of the moving divider. Operation and control of such valves may take various embodiments, as described herein.

The accumulator 32 may be configured to contain less volume of anesthetic agent than the variable volume reservoir 14. In one embodiment, the variable volume reservoir is configured to contain a maximum volume of liquid anesthetic agent in the range of 250 ml to 350 ml, and in one particular example is configured to contain a maximum of approximately 300 ml of liquid anesthetic agent. Given that the variable volume reservoir may be a flexible volume, such as an elastomeric balloon, the variable volume reservoir 14 may not have a precisely fixed maximum volume but may instead be configured to easily accommodate a maximum volume of liquid anesthetic agent. The sump chamber 12, being a rigid chamber, has a fixed maximum volume. For example, the maximum volume for the sump chamber 12 may be in the range of 300 ml-400 ml. To provide one specific example, the sump chamber 12 may have an interior volume of 340 ml; however, a person having ordinary skill in the art will understand that the sump chamber may be larger or smaller as demanded by the particular anesthetic vaporizer system 1 design.

In various embodiments, the accumulator 32 is configured to contain sufficient volume in order to provide anesthetic agent to the vaporizer throughout the fill process, which is typically in the range of 50-70 seconds, but may be longer or shorter. The accumulator 32 may thus be sized based on the expected refill time for the particular anesthesia reservoir 10. In one exemplary embodiment, the accumulator is configured to contain a maximum volume in the range of 25 mL to 60 mL. For instance, in embodiments configured for storing Sevoflurane or Isoflurane, the accumulator 32 volume may be on the smaller end of the range, whereas an accumulator 32 configured for delivery of Desflurane may be toward the upper end of the range.

Figure 5:
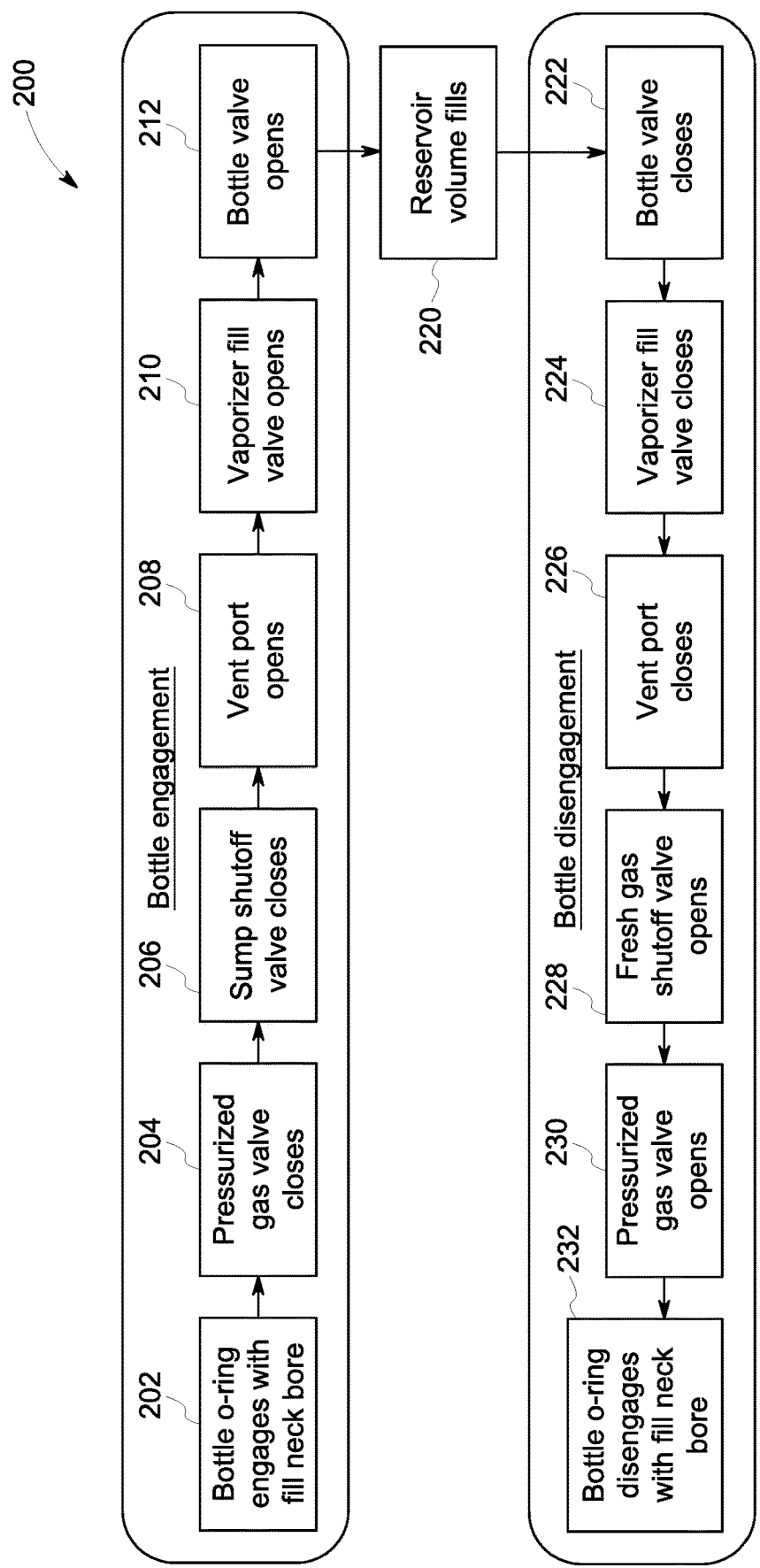
FIG. 5 is a flow chart illustrating one embodiment of a method for refilling an anesthesia reservoir according to one embodiment of the disclosure.

FIG. 5 depicts one embodiment of a method 200 for refilling the anesthesia reservoir 10. As indicated, the steps are divided into bottle engagement steps where an anesthesia bottle 70 is connected to the fill port 22 and bottle disengagement steps where the anesthesia bottle 70 is disconnected from the fill port 22. Between the bottle engagement and bottle disengagement steps, anesthetic agent is evacuated from the bottle into the variable volume reservoir 14, such as by force of gravity. At the first bottle engagement step, the bottle o-ring engages with the fill neck bore at step 202. The pressurized gas valve 24 is then closed at step 204. As described above, actuation of the valve may be caused mechanically by engagement of the bottle with the fill neck bore or may be electrically actuated, such as based on sensor input. The sump shut off valve 28 is then closed at step 206. Actuation of the sump shut off valve may similarly be provided by either mechanical or electrical means. The vent port 26 is then opened at step 208. Various control and actuation means are described herein above. The fill valve of the fill port 22 is then opened at step 210, which again may be by mechanical or electromechanical means. Finally, the bottle valve opens at step 212 which then allows the anesthetic agent therein to flow into the variable volume reservoir 14 at step 220.

Once all of the anesthetic agent has been transferred to the variable volume reservoir 14, or the variable volume reservoir is otherwise at maximum capacity, the bottle disengagement steps are executed. The bottle valve closes at step 222 and then the vaporizer fill valve closes at step 224. The vent port 26 is then closed at step 228, followed by opening the pressurized gas valve at step 230 in order to repressurize the sump chamber 12. Finally, the bottle is removed and the bottle o-ring disengages from the fill neck bore at step 232.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:
1. An anesthesia vaporizer system comprising:
a sump chamber;
a variable volume reservoir within the sump chamber, wherein the variable volume reservoir is configured to contain liquid anesthetic agent;
an anesthetic vaporizer that vaporizes the liquid anesthetic agent for delivery to a patient;
a gas mixer configured to combine gasses from multiple gas sources;
a pressurized gas source connected to the sump chamber and the gas mixer, the pressurized gas source being configured to provide a constant pressure within the sump chamber to compress the variable volume reservoir and force the liquid anesthetic agent through the anesthetic vaporizer; and
a dual outlet valve having an inlet connected to the pressurized gas source, a first outlet connected to the gas mixer, and a second outlet connected to the sump chamber, wherein the dual outlet valve controls flow of gas to the gas mixer and the sump chamber.

2. The anesthesia vaporizer system of claim 1, wherein the variable volume reservoir within the sump chamber is formed by one of a bag, an elastomeric balloon, or a bellows.

3. The anesthesia vaporizer system of claim 1, wherein the variable volume reservoir is formed by a moving divider within the sump chamber, wherein the pressurized gas source is on a first side of the divider and the liquid anesthetic agent is on a second side of the divider.

4. The anesthesia vaporizer system of claim 1, further comprising a sump shutoff valve that opens to permit the liquid anesthetic agent to flow from the variable volume reservoir to the anesthetic vaporizer and closes to prevent the flow of the liquid anesthetic agent from the variable volume reservoir to the anesthetic vaporizer.

5. The anesthesia vaporizer system of claim 4, wherein the sump shutoff valve is closed during refilling of the variable volume reservoir with anesthetic agent.

6. The anesthesia vaporizer system of claim 5, further comprising an accumulator between the sump chamber and the anesthetic vaporizer, wherein the accumulator is configured to accumulate liquid anesthetic agent when the sump shutoff valve is open and to provide the accumulated liquid anesthetic agent to the anesthetic vaporizer when the sump shutoff valve is closed during the refilling of the variable volume reservoir.

7. The anesthesia vaporizer system of claim 6, wherein the accumulator is a second variable volume reservoir.

8. The anesthesia vaporizer system of claim 1, wherein the pressurized gas source is a fresh gas line in an anesthesia machine.

9. The anesthesia vaporizer system of claim 1, wherein the pressurized gas source is a gas canister.

10. The anesthesia vaporizer system of claim 1, further comprising a fill port configured to permit flow of liquid anesthetic agent from a liquid anesthetic agent source to refill the variable volume reservoir.

11. The anesthesia vaporizer system of claim 10, wherein the fill port is integrated with a pressurized gas valve connecting between the pressurized gas source and the sump chamber such that opening the fill port causes the pressurized gas valve to close.

12. The anesthesia vaporizer system of claim 10, further comprising a vent port configured to vent gas from the sump chamber to reduce pressure therein when the variable volume reservoir is refilled.

13. The anesthesia vaporizer system of claim 12, wherein the fill port and the vent port are integrated such that opening the fill port causes the vent port to open.

14. An anesthesia vaporizer system, comprising:
an anesthesia reservoir comprising:
  a sump chamber;
  a variable volume reservoir within the sump chamber, wherein the variable volume reservoir is configured to contain liquid anesthetic agent; and
  a pressurized gas valve configured to connect a pressurized gas source to the sump chamber so as to maintain a constant pressure within the sump chamber to compress the variable volume reservoir and force the liquid anesthetic agent through an anesthetic vaporizer such that the liquid anesthetic agent is vaporized for delivery to a patient;
  a fill port configured to permit flow of liquid anesthetic agent from a liquid anesthetic agent source to refill the variable volume reservoir; and
  a vent port configured to vent gas from the sump chamber when the variable volume reservoir is refilled; and
a gas mixer configured to combine gasses from multiple gas sources; and
a dual outlet valve having an inlet connected to the pressurized gas source, a first outlet connected to the gas mixer, and a second outlet connected to the sump chamber,
wherein the dual outlet valve controls flow of gas to the gas mixer and the sump chamber.

15. The anesthesia reservoir of claim 14, wherein the variable volume reservoir is formed by one of a bag, an elastomeric balloon, or a bellows.

16. The anesthesia reservoir of claim 14, wherein the variable volume reservoir is formed by a moving divider within the sump chamber, wherein the pressurized gas source is on a first side of the divider and the liquid anesthetic agent is on a second side of the divider.

17. The anesthesia reservoir of claim 14, wherein the pressurized gas valve is configured to connect to a fresh gas line in an anesthesia machine.

18. The anesthesia reservoir of claim 14, wherein the pressurized gas valve is configured to connect to a gas canister.

19. The anesthesia reservoir of claim 14, further comprising an accumulator between the sump chamber and the anesthetic vaporizer, wherein the accumulator is configured to accumulate liquid anesthetic agent and to provide the accumulated liquid anesthetic agent to the anesthetic vaporizer when variable volume reservoir is being refilled.

* * * * *